United States Patent
Chang et al.

(10) Patent No.: US 7,649,102 B2
(45) Date of Patent: Jan. 19, 2010

(54) PROPYLENE OXIDE PROCESS

(75) Inventors: Te Chang, West Chester, PA (US);
Arsam Behkish, King of Prussia, PA (US);
Jude T. Ruszkay, Coatesville, PA (US);
John H. Speidel, Jr., Media, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 3 days.

(21) Appl. No.: 12/079,823

(22) Filed: Mar. 28, 2008

(65) Prior Publication Data

US 2009/0247773 A1    Oct. 1, 2009

(51) Int. Cl.
*C07D 301/06* (2006.01)
(52) U.S. Cl. ...................................... 549/533
(58) Field of Classification Search ................... 549/533
See application file for complete search history.

(56) References Cited

U.S. PATENT DOCUMENTS

| | | | |
|---|---|---|---|
| 4,954,325 A | 9/1990 | Rubin et al. | |
| 5,973,171 A | 10/1999 | Cochran et al. | |
| 6,077,498 A | 6/2000 | Diaz Cabañas et al. | |
| 6,114,551 A | 9/2000 | Levin et al. | |
| 6,624,319 B2 * | 9/2003 | Hofen et al. | 549/541 |
| 7,138,535 B1 | 11/2006 | Whitman et al. | |
| 7,238,817 B1 | 7/2007 | Han | |
| 7,279,145 B2 | 10/2007 | Balan | |
| 2003/0031624 A1 * | 2/2003 | Schummer et al. | 423/651 |

FOREIGN PATENT DOCUMENTS

BE    1001038 A7    6/1989

OTHER PUBLICATIONS

R. Szostak, "Non-aluminosilicate molecular sieves" in Molecular sieves: Principles of synthesis and identification (1989), pp. 205-282, Van Nostrand Reinhold.
G. Vayssilov, "Structural and physicochemical features of titanium silicalites" in Catal., Rev.-Sci. Eng., (1997), pp. 209-251, vol. 39 (3).
T. Maschmeyer et al., "Heterogeneous catalysts obtained by grafting metallocene complexes onto mesoporous silica" in Nature, (Nov. 1995), p. 159, vol. 378 (9).
P. T. Tanev et al., "Titanium-containing mesoporous molecular sieves for catalytic oxidation of aromatic compounds" in Nature, (Mar. 1994), p. 321, vol. 368.
A. Corma et al., J. Chem. Soc., Chem. Commun., (1998), p. 579.
D. Wei et al., "Catalytic behavior of vanadium substituted mesoporous molecular sieves" in Catal. Today, (1999), pp. 501-511, vol. 51.
Y. T. Shah et al., "Design parameters estimations for bubble column reactors" in AIChE Journal, (May 1982), pp. 353-379, vol. 28 (3).

* cited by examiner

*Primary Examiner*—Bernard Dentz
*Assistant Examiner*—David E Gallis
(74) *Attorney, Agent, or Firm*—Yuanzhang Han

(57) ABSTRACT

A process for making propylene oxide from propylene is disclosed. Propylene, hydrogen, and oxygen are reacted in a slurry comprising a catalyst and a solvent to produce a gaseous product stream and a liquid product stream. The gaseous product stream is contacted with an absorbent to produce a gas effluent and a liquid effluent. The gas effluent is recycled to the reaction step.

15 Claims, 1 Drawing Sheet

PROPYLENE OXIDE PROCESS

FIELD OF THE INVENTION

The invention relates to a process for producing propylene oxide by reacting propylene, oxygen, and hydrogen in a slurry comprising a catalyst and a solvent.

BACKGROUND OF THE INVENTION

Propylene oxide is an important industrial chemical intermediate. Propylene oxide can be produced by direct oxidation of propylene with oxygen and hydrogen in a solvent in the presence of a catalyst (U.S. Pat. Nos. 7,138,535; 7,238,817; 7,279,145; and 5,973,171).

The copending application Ser. No. 11/728,098, filed on Mar. 23, 2007, teaches that a propylene oxide reaction product mixture stream comprising propylene oxide, solvent, propylene, propane, and various oxygenated materials is passed from a propylene oxide producing reaction unit to a flash separator wherein the mixture is flashed to form separate vapor and liquid phases. From the separator a vapor fraction is passed to a propylene oxide absorber wherein propylene oxide is absorbed into an absorption methanol/water liquid. The overhead vapors from the absorber are recycled to the propylene oxide reaction system with a small portion being sent to a vent recovery system.

Propylene oxide produced in the direct oxidation often further reacts with the solvent such as water and an alcohol in the reactor to form byproducts such as propylene glycol, dipropylene glycol, and propylene glycol ethers. This invention reduces the formation of such byproducts.

SUMMARY OF THE INVENTION

The invention is a process for making propylene oxide from propylene. The process comprises reacting propylene, oxygen, and hydrogen in a slurry comprising a catalyst and a solvent to produce a gaseous product stream and a liquid product stream. The gaseous product stream is contacted with an absorbent to produce a gas effluent and a liquid effluent. The gas effluent is recycled to the reaction step.

DETAILED DESCRIPTION OF THE INVENTION

Figure 1:
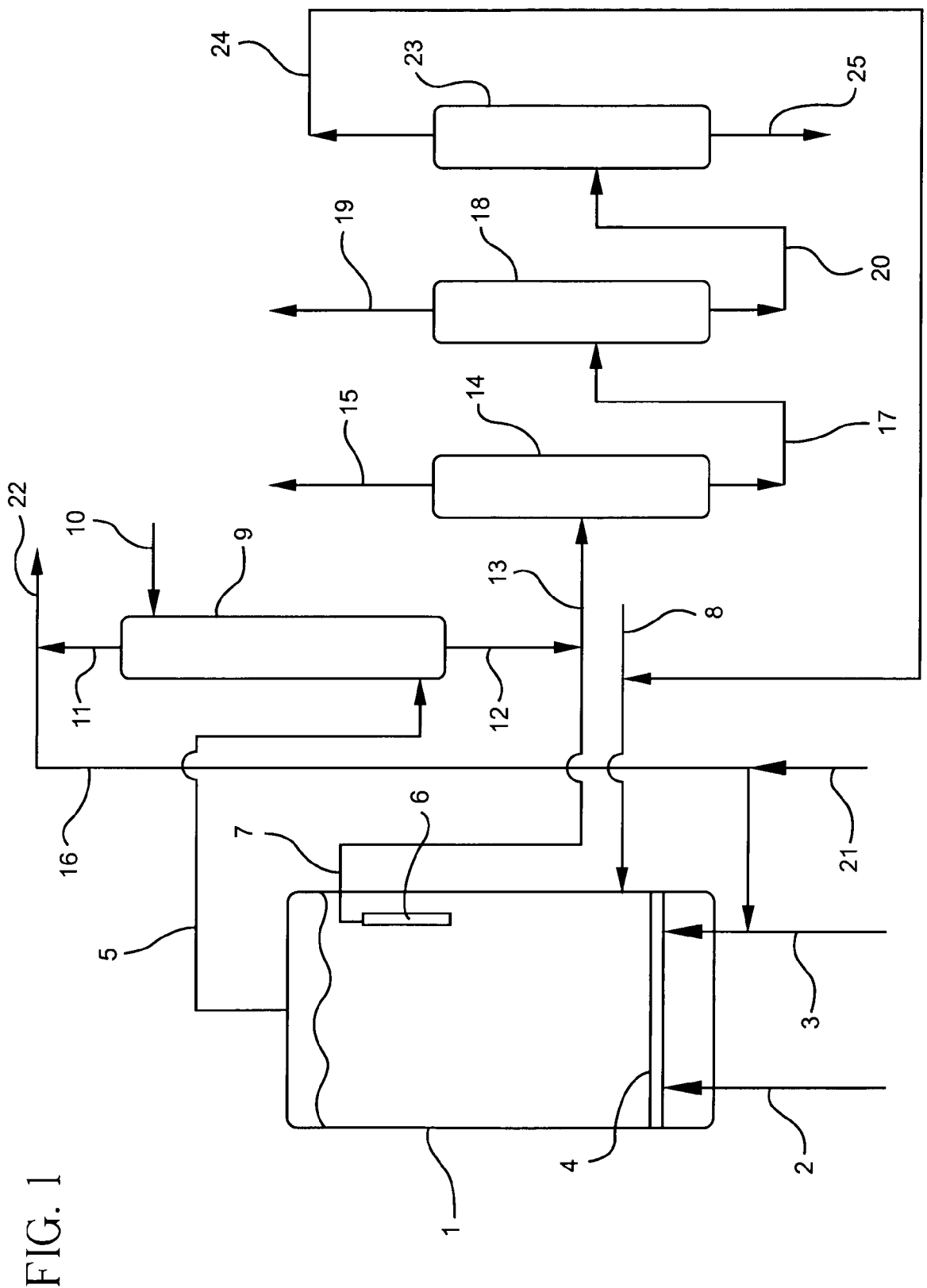
FIG. 1 is a schematic presentation of one embodiment of the present invention.

The process comprises reacting propylene, oxygen, and hydrogen in a slurry comprising a catalyst ("the reaction step"). A suitable catalyst comprises a transition metal zeolite and a noble metal. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of these includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the olefin to be epoxidized. For example, it is especially advantageous to use titanium silicalite-1 (TS-1, a titanium silicalite having an MFI topology analogous to that of the ZSM-5 aluminosilicate) for the epoxidation of propylene. For a bulky olefin such as cyclohexene, larger pore zeolites may be preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and mixtures thereof, may be present in the lattice. The amount of impurities is preferably less than 0.5 weight percent (wt %), more preferably less than 0.1 wt %. Preferred titanium silicates will generally have a composition corresponding to the following empirical formula: $xTiO_2 \cdot (1-x)SiO_2$, where x is between 0.0001 and 0.5. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Tanev, P. T., et al., *Nature* 368 (1994) 321; Corma, A., *J. Chem. Soc., Chem. Commun.* (1998) 579; Wei D., et al., *Catal. Today* 51 (1999) 501). The most preferred is TS-1.

Suitable noble metals include, e.g., gold, silver, platinum, palladium, iridium, ruthenium, rhenium, rhodium, osmium, and mixtures thereof. Preferred noble metals are Pd, Pt, Au, Re, Ag, and mixtures thereof. A catalyst comprising palladium is particularly preferred. Typically, the amount of noble metal present in the epoxidation catalyst will be in the range of from 0.01 to 20 wt %, preferably from 0.1 to 5 wt %.

The noble metal and the transition metal zeolite may be on a single particle or on separate ones. For example, the noble metal may be supported on the transition metal zeolite. Alternatively, the catalyst may comprise a mixture of a transition metal zeolite and a noble metal supported on a carrier. Suitable carriers for the supported noble metal include carbons, titanias, zirconias, niobias, silicas, aluminas, silica-aluminas, titania-silicas, ion-exchange resins, and the like, and mixtures thereof.

The manner in which the noble metal is incorporated into the catalyst is not critical. For example, the noble metal may be supported on the transition metal zeolite or other carriers by impregnation, ion exchange, adsorption, precipitation, or the like.

The weight ratio of the transition metal zeolite to the noble metal is not particularly critical. However, a transition metal zeolite to noble metal ratio of 10-10000 (grams of transition metal zeolite per gram of noble metal) is preferred.

The catalyst particles are generally very small in size and have a mean mass diameter of from 10 to 500 μm, preferably from 20 to 100 μm. Catalyst particles of this size range can be produced by a number of means, one example of which is spray drying. Use of a catalyst of such size minimizes the mass transfer between the liquid and the catalyst due to large solid-liquid interfacial area.

The concentration of the catalyst in the slurry is typically in the range of from 1 to 40 wt %, preferably in the range of from 5 to 30 wt %.

The process uses propylene. Any gas comprising propylene may be used. Typically, it comprises greater than 90 wt % propylene. Preferably, it comprises greater than 95 wt % propylene.

The process uses oxygen. Any gas comprising oxygen may be used. Typically, it comprises greater than 10 wt % oxygen. Preferably, it comprises greater than 90 wt % oxygen.

The process uses hydrogen. Any gas comprising hydrogen may be used. Typically, it comprises greater than 10 wt % hydrogen. Preferably, it comprises greater than 90 wt % hydrogen.

The molar ratio of hydrogen to oxygen can usually be varied in the range of $H_2:O_2=1:100$ to 10:1 and is especially favorable at 1:5 to 2:1. The molar ratio of oxygen to propylene is usually 1:1 to 1:20, and preferably 1:1.5 to 1:10.

In addition to propylene, oxygen, and hydrogen, an inert gas may be used. Suitable inert gases include nitrogen, helium, argon, and carbon dioxide. Saturated hydrocarbons with 1-4 carbon atoms, e.g., methane, ethane, propane, and n-butane, may be used. Mixtures of the listed inert gases can be used. The molar ratio of olefin to inert gas is usually in the range of 100:1 to 1:20 and especially 20:1 to 1:20.

The process uses a solvent. Suitable solvents are liquid under the reaction conditions. They include, for example, oxygen-containing hydrocarbons such as alcohols, aromatic and aliphatic solvents such as toluene and hexane, nitriles such as acetonitrile, and water. Suitable oxygenated solvents include alcohols, ethers, esters, ketones, water, and the like, and mixtures thereof. Preferred oxygenated solvents include water, methanol, ethanol, isopropanol, tert-butanol, and mixtures thereof. Particularly preferred oxygenated solvents are selected from the group consisting of water, methanol, and mixtures thereof.

The process may use a buffer. The buffer is employed in the reaction to inhibit the formation of propylene glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphates, and ammonium hydroxide. The ammonium phosphates buffer is particularly preferred.

The reaction step is typically performed at a temperature in the range of from 30 to 100° C., preferably in the range of from 50 to 70° C., and at a pressure in the range of from 100 to 800 psig, preferably in the range of from 150 to 400 psig. A cooling coil is preferably used to remove the heat of the reaction.

The reactor content is typically well mixed. Any suitable method for mixing a gas and a slurry may be used. For example, a mechanical agitator can be used.

The reactor content may be mixed solely by a flow of gas bubbles in a slurry bubble-column reactor so that no mechanical agitator is used. Typically three flow regimes have been identified in a slurry bubble-column reactor: homogeneous, heterogeneous (or churn-turbulent), and slug flow regime. See Y. T. Shah, et al., *AIChE Journal* 28(3) (1982) 353-79. The superficial gas velocity and the column diameter are the main variables that determine the flow regime of the slurry bubble-column reactors. The superficial gas velocity is the gas flow rate divided by the internal cross-section area of the bubble column at the reaction conditions. The homogeneous flow regime occurs when the superficial gas velocity is relatively low (e.g., <0.05 meters per second, m/s) and is marked by a narrow bubble-size distribution, and bubbles are distributed relatively uniformly over the cross section of a reactor, a column, or other vessels. In this regime the mixing intensity and axial dispersion are low due to weak bubble-bubble interactions. As the superficial gas velocity increases the uniform distribution of gas bubbles vanishes, and a highly turbulent flow structure appears. This is called a heterogeneous flow (also called churn-turbulent flow) regime, where large bubbles or agglomerates of bubbles form and travel upward at high velocity, mainly in the axis of the vessel. The heterogeneous regime is also dependent on the column diameter and occurs at a certain column diameters typically above 0.10 m depending on the operating conditions and physical properties of the three-phase system. At lower diameter (i.e., <0.10 m) and high superficial gas velocities (e.g., >0.05 m/s) slug flow regime prevails where large bubbles are stabilized by the column wall and take on the characteristic slug shape. In this regime the mixing and mass transfer are very poor.

Preferably, the reaction step is conducted in a slurry bubble-column reactor wherein the reactor content is mixed by gas bubbles in a churn-turbulent flow regime. Due to high gas flow rate and mixing intensity in this regime, there is a significant bubble-bubble interaction that results in a high level of bubble coalescence and break-up. Similarly a bimodal bubble size distribution (large and small gas bubbles) is observed. This is referred to as the two-bubble class mode. The large gas bubbles rise fast in the center of the column in a plug-flow manner and are responsible for the mixing, dispersion and solid suspension, whereas the small gas bubbles with small rise velocity are entrained in the liquid-backmixing and contribute mostly toward the enhancement of the gas holdup and mass transfer.

Propylene, oxygen, and hydrogen are preferably fed to the reactor at or near the bottom of the reactor. More preferably they are fed to the reactor via a gas sparger. The sparging of the gas bubbles is the main mechanism for mixing, catalyst suspension, and dispersion.

The reactor is preferably cylindrical in shape and has a diameter of greater than 0.1 m and has a height-to-diameter ratio of greater than 3:1. The reactor diameter has a significant effect on the flow regime of a slurry bubble-column reactor.

When a slurry bubble-column reactor is used, the superficial gas velocity in the reactor is preferably in the range of from 0.05 to 0.60 m/s. More preferably, it is in the range of from 0.08 to 0.20 m/s.

The process produces a gaseous product stream and a liquid product stream. The reactor has a vapor zone that comprises mostly gaseous components and a slurry zone that comprises the liquid components and the catalyst. The gaseous product stream is removed from the vapor zone of the reactor and the liquid product stream is removed from the slurry zone of the reactor. A filter may be used to filter the slurry so the catalyst remains in the reactor. The filter may be located within the reactor or installed outside of the reactor.

The gaseous product stream is contacted with an absorbent to produce a gas effluent and a liquid effluent. The gaseous product stream exits the reactor from the vapor zone and enters the absorber. An absorbent is any liquid that can absorb propylene oxide from a gas stream. Preferably, the solvent or one of the solvents used in the reaction step is used as the absorbent. More preferably, the absorbent is a recycled solvent from the process (see Example 1). An absorbent comprising methanol is particularly preferred. The gaseous product stream comprises propylene oxide, propylene, propane, hydrogen, oxygen, solvent vapor, and inert gases if used. Preferably the gaseous product stream comprises at least 10 percent, more preferably at least 20 percent, and most preferably at least 30 percent of propylene oxide produced in the reaction step. Typically the absorber is operated at a temperature in the range of 0 to 30° C. and a pressure of from 50 to 500 psig.

The gas effluent comprises propylene, hydrogen, oxygen, propane, solvent vapor, and inert gases if used. Typically, the gas effluent comprises less than 0.1 mol % propylene oxide relative to the total mole of the gas effluent, preferably less than 0.01 mol %.

The gas effluent is recycled to the reactor. The gas effluent may be combined with the fresh hydrogen or propylene to enter the reactor. Alternatively, it enters the reactor via a separate line.

The present process removes propylene oxide from the gaseous product stream instead of recycling the gaseous product stream directly to the reactor, thus reduces the undesired propylene oxide decomposition as a result of the reduced contact between propylene oxide and the slurry.

Following examples merely illustrate the invention. Those skilled in the art will recognize many variations that are within the spirit of the invention and scope of the claims.

EXAMPLE 1

Propylene Epoxidation

The following is one proposed method of practicing the process of the invention.

A catalyst is prepared by following the procedure taught by Example 5 of the copending application Ser. No. 11/891,460, filed on Aug. 10, 2007. The catalyst (3 kg) prepared by using the above procedure is charged to a cylindrical reactor 1 (FIG. 1) with a diameter of 0.20 m and a height of 5.2 m, equipped with two gas spargers (represented by 4) at the bottom, a gas outlet 5 at the top of the reactor, and a liquid inlet 8. An internal filter 6 is installed on the liquid outlet line 7. A cooling coil (not shown) is used to remove the heat of the reaction. Fresh propylene (0.92 kg/h) and hydrogen (660 standard liter per hour, SLPH) are fed to reactor via line 3. Oxygen (600 SLPH) is fed to reactor via line 2. The overall superficial gas velocity (including recycled gases from lines 16 and 21) is 0.15 m/s. A methanol/water mixture (85/15 by weight, flow rate 15 kg/h), recycled from a solvent-recovery unit 23, containing 5 mM ammonium phosphate is fed to the reactor via line 24. The reaction is operated at 60° C. and under pressure of 300 psig. A gaseous product stream exits the reactor via line 5 at a flow rate of 18 kg/h. The gaseous product stream comprises 0.38 mole percent (mol %) propylene oxide (PO), 1.58 mol % propane, 7.9 mol % oxygen, and 1.8 mol % hydrogen. PO is removed from the gaseous product stream through the use of the absorber 9. The absorber 9 has about 20 theoretical stages. A methanol-containing recycled solvent is chilled to 15° C. and fed to the top of the absorber 9 at a flow rate of 6 kg/h via line 10. The gaseous product stream is fed to the bottom of the absorber via line 5. The absorber gas effluent in line 11 after a small purge via line 22 is recompressed (not shown) and recycled to the reactor via line 16. The absorber liquid effluent exits the absorber via line 12. The reactor liquid product stream exits the reactor via line 7 at a flow rate of 16 kg/h. The liquid product stream comprises 3.3 wt % PO, 0.87 wt % propylene, and 74 wt % methanol. The liquid product stream 7 from the reactor and the absorber liquid effluent 12 are combined into a liquid stream 13, which is fed to a depropanizer 14. The depropanizer 14 has 20 theoretical stages. Its overhead temperature is 3° C. and pressure is 10 psig. Its bottoms temperature is 82° C. and pressure is 10.2 psig. A C3 stream, comprising mostly propylene and propane exiting the depropanizer 14 via line 15, is sent to a C3 splitter (a distillation column, not shown) for propylene enrichment before it is recycled to the reactor 1 via line 21. The depropanizer liquid stream 17 is fed to a crude PO column 18. The crude PO column 18 has 44 theoretical stages. Its overhead temperature is 36° C. and pressure is 1 psig. Its bottoms temperature is 74° C. and pressure is 1.4 psig. Crude PO stream is obtained as overhead 19. The remaining liquid stream exits column 18 via line 20. The remaining liquid stream, comprising 72 wt % methanol, 20 wt % water, and derivatives of propylene oxide such as propylene glycol, propylene glycol monomethyl ethers, dipropylene glycol, and dipropylene glycol methyl ethers, is sent to the solvent-recovery column 23 via line 20 for water and heavies removal. Column 23 has 16 theoretical stages. Its overhead temperature is 72° C. and pressure is about 0 psig. Its bottoms temperature is 100.5° C. and pressure is 0.2 psig. A methanol-containing solvent is recovered as overhead and is recycled to the reactor 1 via line 24. Water and heavies are removed via line 25.

The overall PO/POE selectivity is expected to be about 89%. POE represents the total amount of PO and PO equivalents (propylene glycol, dipropylene glycol, and propylene glycol ethers) formed in the process. POE (mole)=moles of PO+moles of PO units in the PO derivatives. PO/POE mole selectivity=(moles of PO)/(moles of POE)×100.

COMPARATIVE EXAMPLE 2

Propylene Epoxidation

The procedure of Example 1 is repeated, except that the gaseous product stream 5 is recycled to the reactor via line 21 and absorber 9 is not used. Additionally, 6 kg/h solvent that is fed to the absorber in Example 1 is now combined with the recycle solvent (15 kg/h) and fed directly to the reactor via line 8. The overall PO/POE mole selectivity is expected to be about 85%, calculated based on the kinetic rate constants of reactions of PO with water and methanol.

We claim:

1. A process for producing propylene oxide comprising
   (a) reacting propylene, oxygen, and hydrogen in a slurry comprising a catalyst and a solvent to produce propylene oxide, wherein the propylene oxide is present in a gaseous product stream and a liquid product stream;
   (b) contacting the gaseous product stream with an absorbent to produce a gas effluent and a liquid effluent; and
   (c) recycling the gas effluent to the step (a).

2. The process of claim 1 wherein the gaseous product stream comprises at least 10 percent of the propylene oxide produced in the step (a).

3. The process of claim 2 wherein the gaseous product stream comprises at least 20 percent of the propylene oxide produced in the step (a).

4. The process of claim 1 wherein the gas effluent comprises less than 0.1 mole percent propylene oxide.

5. The process of claim 1 wherein the gas effluent comprises less than 0.01 mole percent propylene oxide.

6. The process of claim 1 wherein the solvent is selected from the group consisting of water, methanol, and mixtures thereof.

7. The process of claim 1 wherein the absorbent is a recycled solvent from the process.

8. The process of claim 1 wherein the catalyst comprises a transition metal zeolite and a noble metal.

9. The process of claim 1 wherein the catalyst has a concentration in the range of from 5 to 30 wt % relative to the slurry.

10. The process of claim 1 wherein the step (a) is performed in a slurry bubble-column reactor.

11. The process of claim 10 wherein the reactor content is mixed by gas bubbles in a churn-turbulent flow regime.

12. The process of claim 10 wherein the reactor is cylindrical and has a diameter of greater than 0.2 meter and a height-to-diameter ratio of greater than 3:1.

13. The process of claim 10 wherein the propylene, oxygen, and hydrogen are fed at or near the bottom of the reactor.

14. The process of claim 1 wherein the step (a) is performed at a temperature in the range of from 30 to 100° C.

15. The process of claim 1 wherein the step (a) is performed at a pressure in the range of from 150 to 400 psig.

* * * * *